(12) United States Patent
Brantley et al.

(10) Patent No.: US 6,478,969 B2
(45) Date of Patent: *Nov. 12, 2002

(54) SHEAR SEPARATION METHOD AND SYSTEM

(75) Inventors: John D. Brantley, Sound Beach, NY (US); Mark F. Hurwitz, Ithaca, NY (US); Stephen A. Geibel, Cortland, NY (US); Jack Cole, Huntington, NY (US); Mahmoud Reyad, Cortland, NY (US)

(73) Assignee: Pall Corporation, East Hills, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,226
(22) PCT Filed: Sep. 5, 1997
(86) PCT No.: PCT/US97/16656
§ 371 (c)(1),
(2), (4) Date: May 11, 1999
(87) PCT Pub. No.: WO98/09717
PCT Pub. Date: Mar. 12, 1998

(65) Prior Publication Data
US 2002/0038787 A1 Apr. 4, 2002

Related U.S. Application Data
(60) Provisional application No. 60/025,405, filed on Sep. 6, 1996, and provisional application No. 60/047,819, filed on May 28, 1997.

(51) Int. Cl.[7] .......................... B01D 61/00; B01D 63/08
(52) U.S. Cl. .................. 210/651; 210/650; 210/321.67; 210/321.75; 210/331; 210/97; 210/96.2; 210/107

(58) Field of Search .................. 210/651, 650, 210/321.75, 321.67, 330, 321.64, 331, 96.1, 96.2, 106, 107, 97, 360.1, 380.1

(56) References Cited

U.S. PATENT DOCUMENTS 3,128,230 A 4/1964 Heinbech et al. ............. 167/78
3,517,811 A 6/1970 Newfarmer (List continued on next page.)

FOREIGN PATENT DOCUMENTS

GB 2 269 166 2/1994
JP 08280391 10/1996

(List continued on next page.)

OTHER PUBLICATIONS

Merin et al., "Microfiltration of Sweet Cheese Whey", New Zealand Journal of Dairy Science and Tech., vol. 18, 1983, pp. 153–160.
Damerow et al., "Die Anwendung der Mikrofiltration Für Konsummilch, Kesselmilch, Molke", Deutsche Molkerei–Zeitung DMZ, vol. 110, No. 50, Dec. 14, 1989, pp. 1602–1603 and 1606–1608.

(List continued on next page.)

Primary Examiner—Ana Fortuna
(74) Attorney, Agent, or Firm—Leydig, Voit & Mayer, Ltd.

(57) ABSTRACT

A shear separation system or method uses shear lift forces and permeate drag forces to separate substances having a size less than a predetermined separation size from substances having a size greater than the separation size. The balance of the drag forces and lift forces affects a predetermined separation size in that the balance of forces reads the transmembrane passage of substances larger than the separation size yet allows substances smaller than the separation size to pass through the permeable membrane. The shear separation device, method and system can be employed to separate or concentrate from a process fluid substances larger or smaller than the predetermined separation size.

92 Claims, 4 Drawing Sheets

U.S. PATENT DOCUMENTS

| | | | |
|---|---|---|---|
| 3,743,480 A | 7/1973 | Falk | |
| 3,813,289 A | 5/1974 | Huber et al. | |
| 3,883,626 A | 5/1975 | Kamide et al. | 264/49 |
| 3,992,521 A | 11/1976 | LeMinor | 424/157.1 |
| 4,125,527 A | 11/1978 | Buhler et al. | |
| 4,140,806 A | 2/1979 | Glimenius et al. | 426/491 |
| 4,340,591 A | 7/1982 | Lucotte et al. | 424/177 |
| 4,352,695 A | 10/1982 | Tomka | 106/135 |
| 4,407,747 A | 10/1983 | Lippe et al. | 260/120 |
| 4,427,552 A | 1/1984 | Lieberherr et al. | 210/741 |
| 4,462,932 A | 7/1984 | Lonergan | 260/119 |
| 4,644,056 A | 2/1987 | Kothe et al. | 530/387 |
| 4,721,674 A | 1/1988 | Lepienne et al. | 435/206 |
| 4,732,757 A | 3/1988 | Stolle et al. | 424/157.1 |
| 4,755,300 A | 7/1988 | Fischel et al. | 210/650 |
| 4,790,942 A | 12/1988 | Shmidt et al. | 210/650 |
| 4,873,316 A | 10/1989 | Meade | 435/69.1 |
| 4,876,100 A | 10/1989 | Holm et al. | 426/491 |
| 4,897,465 A | 1/1990 | Cordle et al. | 530/387 |
| 4,906,616 A | 3/1990 | Gilchrist et al. | 514/21 |
| 5,008,376 A | 4/1991 | Bottomley | 530/366 |
| 5,075,424 A | 12/1991 | Tanimoto et al. | 530/361 |
| 5,143,630 A | 9/1992 | Rolchigo | 210/780 |
| 5,149,647 A | 9/1992 | Burling | 435/192 |
| 5,167,823 A | 12/1992 | Leighton et al. | 210/637 |
| 5,254,250 A * | 10/1993 | Rolchigo et al. | 210/321.67 |
| 5,256,437 A | 10/1993 | Degen et al. | 426/580 |
| 5,260,057 A | 11/1993 | Cordle et al. | 424/157.1 |
| 5,298,016 A | 3/1994 | Gordon | |
| 5,310,877 A | 5/1994 | Spencer | 530/364 |
| 5,356,651 A | 10/1994 | Degen et al. | 426/491 |
| 5,374,356 A | 12/1994 | Miller et al. | 210/641 |
| 5,401,422 A | 3/1995 | Mignot | 210/781 |
| 5,401,523 A | 3/1995 | Degen et al. | 426/580 |
| 5,468,844 A | 11/1995 | Smith | 530/366 |
| 5,476,995 A | 12/1995 | Clark et al. | 800/2 |
| 5,565,362 A | 10/1996 | Rosen | 435/320.1 |
| 5,578,213 A | 11/1996 | Miller et al. | 210/641 |
| 5,589,604 A | 12/1996 | Droban et al. | 800/2 |
| 5,993,674 A * | 11/1999 | Rochilgo et al. | 210/780 |

FOREIGN PATENT DOCUMENTS

| | | |
|---|---|---|
| NZ | 216567 | 10/1988 |
| NZ | 226344 | 8/1991 |
| NZ | 238751 | 3/1994 |
| NZ | 240725 | 5/1994 |
| NZ | 248417 | 7/1994 |
| NZ | 245929 | 12/1994 |
| WO | WO 85/04112 | 9/1985 |
| WO | WO 92/06765 | 4/1992 |
| WO | WO 92/21425 | 12/1992 |
| WO | WO 94/13148 | 6/1994 |
| WO | WO 95/00231 | 1/1995 |
| WO | WO 96/01676 | 1/1996 |
| WO | WO 97/13571 | 4/1997 |

OTHER PUBLICATIONS

Piot et al., "Microfiltration en flux Tangentiel des Lactesérums de Fromagerie", Le Lait, vol. 64, 1984, pp. 102–120.

Daufin et al., "Ultrafiltration of Defatted Whey: Influence of Some Physicochemical Characteristics", Australian Journal of Dairy Technology, vol. 47, No. 1, May 1992, pp. 7–13.

Levesley et al., "Particulate Separation Using Inertial Lift Forces", Chemical Engineering Science, vol. 48, No. 21, 1983, pp. 3657–3669.

Happel et al., "Low Reynolds Number Hydrodynamics with Special Applications to Particulate Media", Kluwer Academic Publishers, Fifth printing 1991, pp. 220–223.

Ballmann et al., "The Deformation of Dextran Molecules, Causes and Consequences in Ultrafiltration", Journal of Membrane Science, 40 (1989) pp. 311–327.

"How to Keep Your Fluid Processing Budget From Going to Waste", SpinTek Centrifugal Membrane Filtration, Huntington Beach, California, 12 pages.

"Membrane & Seperation Technology News", vol. 10, No. 12, Aug. 1992, pp. 1–3.

SpinTek Centrifugal Membrane Filtration, Press Release, "Spintek Introduces New High Shear Rotary Cross Flow System for Micro and Ultrafiltration", 2 Pages.

Tiu et al., "Steady and Dynamic Shear Properties of Non–Agueous Drag–Reducing Polymer Solutions", Rheoligica Acta, 34(6), 1995, pp. 586–600, Abstract only.

Gordon et al., "Production of Human Tissue Plasminogen Activator in Transgenic Mouse Milk", Bio/Technology, vol. 5, pp. 1183–187, Nov. 1987.

Barash et al., "Co–Integration of β–Lactoglobulin/Human Serum Albumin Hybrid Gene with the Entire β–Lactoglobulin Gene or the Matrix Attachment Region Element . . . ", Molecular Reproduction and Development, vol. 45, pp. 421–430, 1996.

Clark et al., "Expression of Human Anti–Hemophilic Factor IX in the Milk of Transgenic Sheep", Bio/Technology, vol. 7, pp. 487–492, May 1989.

Ebert et al., "Induction of Human Tissue Plasminogen Activator in the Mammary Gland of Transgenic Goats", Bio/Technology, vol. 12, pp. 699–702, Jul. 1994.

Archer et al., "Human Growth Hormone (hGH) Secretion in Milk of Goats after Direct Transfer of the hGH Gene in the Mammary Gland by Using Replication–Defective Retrovirus Vectors", Proc. Natl. Acad. Sci. USA, vol. 91, pp. 6840–6844, Jul. 1994.

Lee et al. "Production of Biomedical Proteins in the Milk of Transgenic Dairy Cows: The State of the Art", J. Control Release vol. 29, pp. 213–221, 1994 (Abstract only).

Archibald et al., "High–Level Expression of Biologically Active Human $\alpha_1$ –Antitrypsin in the Milk of Transgenic Mice", Proc. Natl. Acad. Sci. USA, vol. 87, pp. 5178–5182, Jul. 1990.

Biotechnology Newswatch, "Gene Altered Cows Successfully Produce Human Collagen in Milk", Feb. 17, 1997, p. 3, Abstract.

Biotechnology Newswatch, "Production of Recombinant Polypeptides by Bovine Species and Transgenic Methods", Jan. 6, 1997, Patentwatch; European Patents; p. 5, Abstract.

Biotechnology Newswatch, Genzyme Bristol–Myers Fete Birth of Goat with Gene for Cancer Antibody, Apr. 15, 1996, Abstract.

Biotechnology Newswatch, "Transgenic Production of Antibodies in Milk", Patentwatch, European Patents, p. 8, Nov. 6, 1995, Abstract.

Biotechnology Newswatch, "Production of Recombinant Polypeptides by Bovine Species and Transgenic Methods", Feb. 21, 1994, Patentwatch, European Patents, p. 6, Abstract.

Biotechnology Newswatch, "Expression of Active Human Protein C in Mammary Tissue of Transgenic Animals", Oct. 5, 1992, Patentwatch, vol. 12, No. 19, p. 7, Abstract.

Biotechnology Newswatch, Genie and Her Four Transgenic Piglets Produce Anti–Clotting Protein in Milk, San Francisco, Apr. 20, 1992, vol. 12, No. 8, p. 12, Abstract.

Biotechnology Newswatch, "Transgenic Rates Produce Human Growth Hormone", Jan. 6, 1992, Japanwatch, vol. 12, No. 1, p. 9, Abstract.

Biotechnology Newswatch, "Goats, Sheet, Cattle Carry Genes for Human Proteins", Sep. 2, 1991, vol. 11, No. 17, p. 1, Abstract.

Biotechnology Newswatch, "Genzyme Creates Oncology Division", Feb. 17, 1987, Business Briefs, p. 14, Abstract.

Biotechnology Newswatch, "Future Bioreactors may be Found in the Barnyard . . . " Jun. 20, 1994, p. 11, Abstract.

Biotechnology Newswatch, "Production of Human Recombinant Collagen in the Milk of Transgenic Animals", Oct. 3, 1994, Patentwatch, European Patent Applications, p. 7, Abstract.

Biotechnology Newswatch, "Genzyme Transgenics Buys Farm, Grazing Land for Drug–Making Goats", May 16, 1994, p. 5, Abstract.

Biotechnology Newswatch, "Transgenic Animals Form Basis for Biopharmaceutical Generic Industry", Nov. 15, 1993, p. 9, Abstract.

Biotechnology Newswatch, "Bayer Puts $18 Million into Drug–Rich Sheep Milk", Business Briefs, Mar. 16, 1992, vol. 12, No. 6, p. 14, Abstract.

Biotechnology Newswatch, "Milk–Antibody Product Could Offer Protection vs. Traveler's Diarrhea", May 20, 1996, p. 11, Abstract.

Biotechnology Newswatch, Biobusiness, Nov. 4, 1985, vol. 5, No. 21, p. 4, Abstract.

Biotechnology Newswatch, "Cystic Fibrosis Drug From Transgenic Sheep Milk Enters Safety Studies", Feb. 17, 1997, p. 4.

Maubois, J.L. et al., "Industrial Fractionation of Main Whey Proteins", Dsiry Research Laboratory, pp. 1–23.

* cited by examiner

FIG. 2a
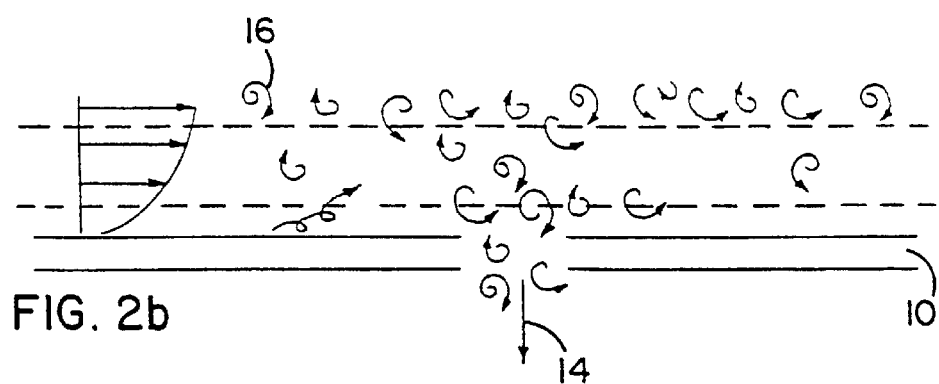
FIG. 2b
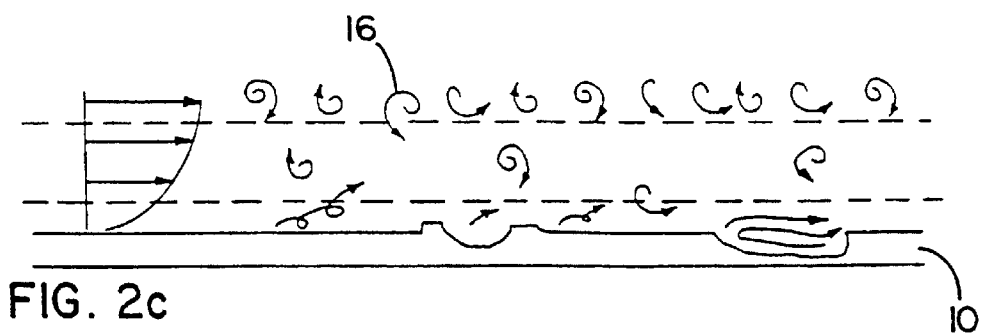
FIG. 2c
FIG. 4
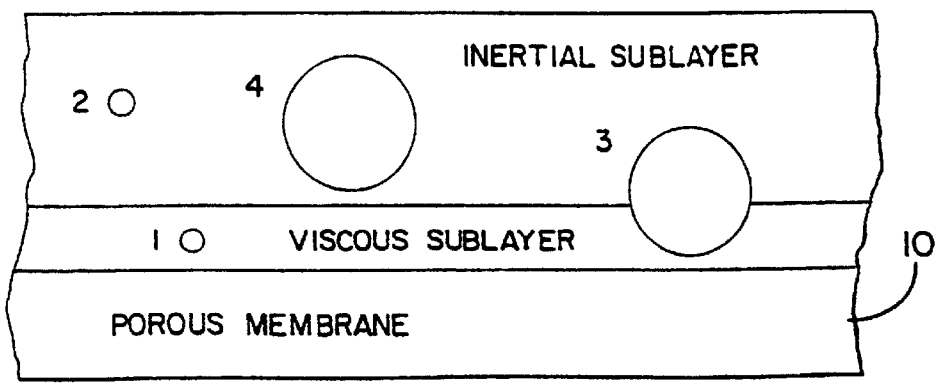

SHEAR SEPARATION METHOD AND SYSTEM

This is a application which claims benefit of Provisional Application Serial No. 60/025,405 filed Sep. 6, 1996 and Serial No. 60/047,819 filed May 28, 1997.

FIELD OF THE INVENTION

The present invention relates to shear separation methods and systems and, more particularly, to shear separation methods and systems wherein microfiltration, ultrafiltration, diafiltration, or concentration can be achieved.

BACKGROUND OF THE INVENTION

Separation methods and systems, such as those employing filters, typically are employed to separate one or more components or substances of a fluid from other components or substances in the fluid. As used herein, the term "fluid" includes liquids, gases, and mixtures and combinations of liquids, gases and/or solids. Conventional separation processes include a wide variety of common processes, such as classic or particle filtration, microfiltration, ultrafiltration, nanofiltration, reverse osmosis (hyperfiltration), dialysis, electrodialysis, prevaporation, water splitting, sieving, affinity separation, purification, affinity purification, affinity sorption, chromatography, gel filtration, bacteriological filtration, and coalescence. Typical separation devices and systems may include dead end filters, cross-flow filters, dynamic filters, vibratory separation systems, disposable filters, regenerable filters including backwashable, blowback and solvent cleanable, and hybrid filters which comprise different aspects of the various above described devices.

Accordingly, as used herein, the term "separation" shall be understood to include all processes, including filtration, wherein one or more components of a fluid is or are separated from the other components of the fluid. The terms "filter", "separation medium", and "permeable membrane" shall be understood to include any medium made of any material that allows one or more substances in a fluid to pass therethrough in order to separate those substances from the other components of the fluid. The terminology utilized to define the various substances in the fluid undergoing separation and the products of these processes may vary widely depending upon the application, e.g., liquid or gas filtration, and the type of separation system utilized, e.g., dead end or open end systems; however, for clarity, the following terms shall be utilized. The fluid which is input to the separation system shall be referred to as process fluid and construed to include any fluid undergoing separation. The portion of the fluid which passes through the separation medium shall be referred to as permeate and construed to include filtrate as well as other terms. The portion of the fluid which does not pass through the separation medium shall be referred to as retentate and construed to include concentrate, bleed fluid, as well as other terms.

While many separation applications are quite routine, the separation of relatively small particles or substances from fluids requires separation protocols able to achieve a precise separation size (resolution) with minimal fouling (e.g., clogging with the small particles). This is particularly the situation when separating proteins (natural or recombinant) and other components from process fluids such as milk or products derived from milk (e.g., skim milk, whey, etc.).

Milk contains, among other things, fats, proteins (casein and a variety of other proteins such as β-lactoglobulin, α-lactalbumin, serum albumin, and immunoglobulins), salts, sugar (lactose), and various vitamins (such as vitamins A, C, and D, along with some B vitamins) and minerals (primarily calcium and phosphorus). The composition of milk varies with the species, breed, feed, and condition of the animal from which the milk is obtained. Moreover, a wide variety of milk or whey proteins are employed as functional and nutritional ingredients in bakery products, pasta, confections, beverages, meats, and other food products. In addition, milk has proven a valuable source of biologically or medically important products. For example, it is possible to obtain antibodies by vaccinating lactating animals and collecting antibodies from their milk (see, e.g., U.S. Pat. Nos. 5,260,057 (Corcle et al.) and 3,128,230 (Heinbach et al.)). Moreover, many species of animals have been genetically engineered to express recombinant proteins in milk. See, e.g., Gordon et al., *Biotechnology*, 5(11), 1183–87 (1987) (mice); Ebert et al., *Biotechnology*, 12(7), 699–702 (1994) (goats); Lee et al., *J. Control. Release*, 29(3), 213–21 (1994) (dairy cows); Limonta et al., *J. Biotechnol.*, 40(1), 49–58 (1995) (rabbits); Clark et al., *Biotechnology*, 7(5), 487–92 (1989) (sheep).

Examples of such recombinant proteins are peptide hormones (e.g., growth hormones (Archer et al., *Proc. Nat. Acad. Sci. USA*, 91(15), 6840–44 (1994)), tissue plasminogen activator (tPA) (Ebert et al., supra), etc.), blood coagulation factors or subunits of them (e.g., factors VIII and IX (Clark et al., supra)), anticoagulation factors or subunits of them (e.g., anti-thrombin III and human protein C), other blood proteins (e.g., serum albumin (Barash et al., *Mol. Repro. Dev.*, 45(4), 421–30 (1996)), beta-globin, α1-antitrypsin (Archibald et al, *Proc. Nat. Acad. Sci. USA*, 87(13), 5178–82 (1990)), proteins for foodstuffs, enzymes, and other proteins (e.g., collagen, cystic fibrosis transmembrane conductance regulator (CFIR), antibodies, etc.). See, e.g., U.S. Pat. No. 4,873,316 (Meade et al.), U.S. Pat. No. 5,589,604 (Drohan et al.), and U.S. Pat. No. 5,476,995 (Clark et al.). Secretion of recombinant proteins into the milk of transgenic animals is an efficient method of producing such proteins; concentrations approaching 10 g/l have been reported.

Commercially produced milk commonly undergoes pasteurization to mitigate bacterial growth and homogenization to improve fat dispersion stability. Moreover, in the commercial processing of milk products, it is desirable in certain instances to remove as much fat as possible from the milk products.

Conventional milk processing heretofore has involved the use of mechanical separation (centrifugation), evaporation/crystallization, steam injection, electrodialysis, reverse osmosis, ultrafiltration, gel filtration, diafiltration, and/or ion exchange chromatography. For example, whey typically is subjected to mechanical separation (e.g., centrifuged) to remove fat, condensed via evaporation to increase solids content, and then spray dried or used for lactose crystallization. After desludging, the residual concentrate is dried, which yields whey powder containing about 11–14% protein (which usually is denatured, particularly during the evaporation/condensation step). The whey powder can be subjected to electrodialysis to remove ash and thereby prepare demineralized whey powder. Alternatively, the whey powder can be subjected to reverse osmosis to remove water, thereby obtaining whey powder containing about 12–15% protein. Such a whey powder can be subjected to ultrafiltration or gel filtration to remove further ash and lactose and thereby obtain a whey protein concentrate containing about 30–50% protein, which, in turn, can be subjected to diafiltration or ion exchange chromatography to remove yet more ash and lactose so as to obtain whey protein concentrates containing about 50–90% protein.

Such conventional processing methods carry with them many disadvantages, such as long processing times, high costs, and poor or inconsistent component fractionation. Moreover, it is often difficult to separate a recombinant protein from fluids such as milk by these methods without denaturing or damaging the protein, and it is also difficult to separate different proteins and particles of interest within milk or other fluids. Many of these difficulties are attributable to the aforementioned problems attendant with separating relatively small particles from fluids, namely poor resolution and filter fouling.

One advancement greatly reducing filter fouling is to employ separation methods and systems generating a shear layer at the surface of a filter. A layer of fluid which is adjacent to the surface of a filter and which is in a state of rapid shear flow parallel to the surface of the filter tends to minimize fouling of the filter by sweeping contaminant matter in the process fluid from the filter. Generally two such technologies can be used for developing a shear layer: cross flow and dynamic filtration. In cross flow systems, high volumes of fluid are driven through passages bounded by the filter surface and possibly the inner surface of the filter housing, thereby creating the necessary shear. Simply stated, process fluid is pumped across the upstream surface of the filter at a velocity high enough to disrupt and back mix the boundary layer. In dynamic filter systems, the necessary shear is created by motion of one or more surfaces that can be provided for that purpose (e.g., the filter surface, the filter vessel, or any contained discs, impellers, etc.). Two widely used configurations are cylinder devices and disc devices. Unlike cross flow filtration systems, the shear created in dynamic filtration systems at the fluid interface is substantially or nearly independent of any cross flow fluid velocity. Traditional cross-flow filtration systems generate shear generally between about 5,000 $sec^{-1}$ and about 10,000 $sec^{-1}$, while shears generated by dynamic filtration systems are between about 100,000 $sec^{-1}$ and about 500,000 $sec^{-1}$.

While dynamic and traditional cross-flow filtration systems can achieve reduced fouling, the size or molecular weight cutoff of the particles of interest is controlled by the separation medium. In both systems, the actual separation or filtering action is effected by the separation medium, the pores of which are sized to remove or separate the particles of interest. Particles larger than the pores are unable to pass through the separation medium while particles smaller than the pores readily pass through the medium. Due to the fouling characteristics of a process fluid and the inherent difficulties in engineering filter media with uniform and predefined pore sizes, high resolution separation of relatively small particles (e.g., molecular weight particles) has been exceedingly difficult using dynamic and cross flow filtration systems.

To address these drawbacks, there is a need for improved means for separating small substances from a solution or a suspension, even a highly fouling solution or suspension. In particular, there is a need for means of effectively concentrating particles of a given molecular weight (e.g., specific proteins), thereby achieving fractionation of such solutions or suspensions. The present invention provides a reliable and efficient means for the separation of small particles or substances (e.g., molecular size particles) from a variety of fluids (e.g., solutions, suspensions, emulsions, etc.), especially milk products.

SUMMARY OF THE INVENTION

The present invention provides shear separation systems and methods for treating a process fluid to separate substances having a size less than a predetermined separation size from substances having a size greater than the separation size. Permeate flow through a permeable membrane establishes a drag force acting on substances upstream of the permeable membrane, and a shear rate is created at the surface of the permeable membrane to establish a lift force acting on substances upstream of the permeable membrane. The balance of the drag force and lift force effects the predetermined separation size in that the balance of forces retards the transmembrane passage of substances larger than the separation size yet allows substances smaller than the separation size to pass through the permeable membrane. Shear separation systems and methods embodying the invention can be employed to separate or concentrate from a process fluid substances larger or smaller than the predetermined separation size by collecting them from the retentate or permeate.

The present invention effects the separation or concentration of relatively small particles or substances, such as proteins and other biological molecules, far more effectively and with much greater flexibility than conventional systems or methods. Therefore, the separation methods and systems of the present invention are useful for the efficient separation of substances from a wide variety of fluids. For example, the present invention can treat milk products to reduce the bacteria and fat therein and/or to recover proteins therefrom, even fractionating such fluids. These and other advantages of the present invention, as well as additional inventive features, will be apparent from the drawings and the detailed description outlined below.

BRIEF DESCRIPTION OF THE DRAWINGS

FIGS. 2A–2C are diagrammatic representations of the effect of turbulence fluctuations on the feed stream tangential velocity profile across a permeable membrane and the permeate velocity profile emerging from the permeable membrane. FIG. 2A depicts fluctuating velocity in each of three fluid flow regions. FIG. 2B depicts the convection of velocity fluctuations towards the upstream surface of a permeable membrane. FIG. 2C depicts the relative increase in the thickness of the viscous sublayer if the surface of the permeable membrane is not smooth.

FIG. 4 is a diagrammatic representation of the effect of the viscous sublayer on large particles.

DETAILED DESCRIPTION

Figure 1:
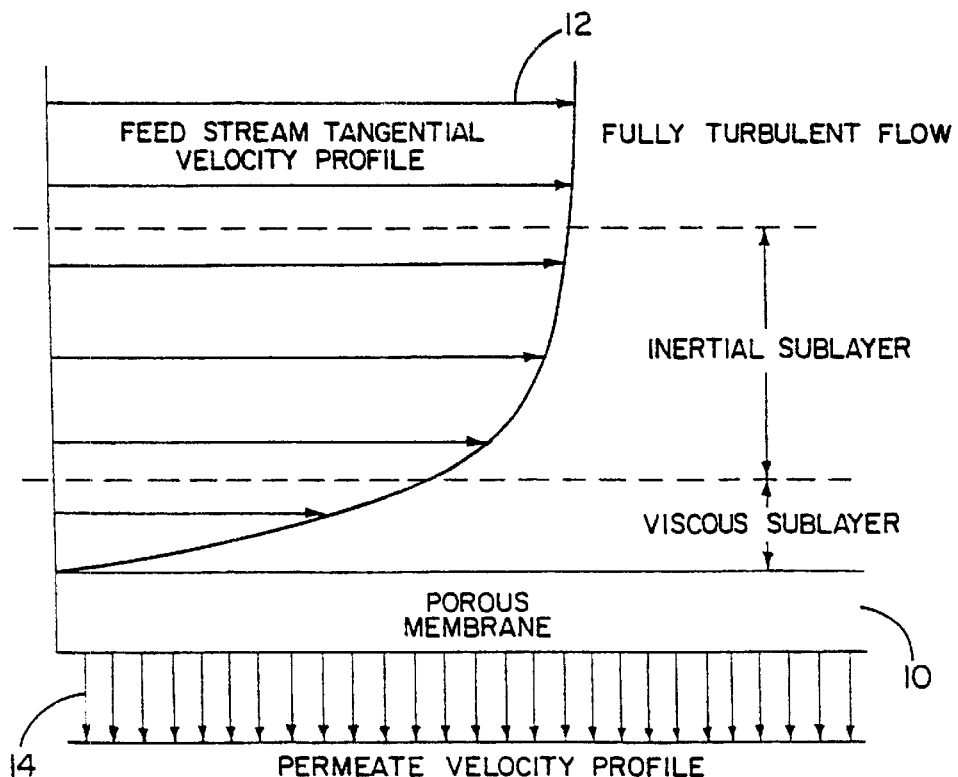
FIG. 1 is a diagrammatic representation of a feed stream tangential velocity profile across a permeable membrane and a permeate velocity profile emerging from the permeable membrane.

The present invention provides shear separation systems and methods of treating a process fluid to separate substances having a size less than a predetermined separation size from substances having a size greater than the separation size by using the shear lift and permeate drag forces which are exerted on the substances near the surface of a permeable membrane to effect the separation. Consequently, the present invention is directed to shear separation systems and methods in which high shear forces generated in a process fluid are used, not merely to prevent fouling of a permeable membrane, but also to separate, by size, substances in the process fluid.

The theory of operation described below is believed to be the mechanism through which the shear separation systems, methods, and devices of the present invention operate. However, other factors or phenomena not described can in some manner affect the shear separation. In addition, other theories of operation may be equally applicable to explain the gross effect achieved by the shear separation systems, methods, and devices of the present invention.

Fluid flow in a direction tangential to a surface produces a region of shear flow in proximity to the surface. The character of the shear flow depends upon the character of the surface and the velocity of the flow. A body or substance suspended in a shear flow near a surface, such as a permeable membrane, experiences a force, i.e., a shear lift force, that tends to drive it away from the surface. The magnitude of this force depends on the character of the shear flow, the size of the suspended body, and the distance of the body from the surface. These phenomena are well known and documented in the fluid mechanics literature. The characteristics of shear flows are described and analyzed in, for example, Schlichting, H., *Boundary Layer Theory.* 7th ed. New York: McGraw-Hill, 1979, and Tennekes, H., and Lumley, J. L., *A First Course in Turbulence.* Cambridge: MIT Press, 1972. Forces on a body suspended in a shear flow are described and analyzed in, for example, Goldman, A. J., Cox, R. G., Brenner, H. 1967. *Slow Viscous Motion of a Sphere Parallel to a Plane Wall-II Coette Flow, Chemical Engineering Science* 22, Saffman, P. G. 1965 *The Lift on a Small Sphere in a Slow Shear Flow, Journal of Fluid Mechanics,* 22, part 2, and more recently, Otis, J. R., Altena, F. W., Mahar, J. T., and Belfort, G. 1986. *Measurements of Single Spherical Particle Trajectories with Lateral Migration in a Slit with One Porous Wall Under Laminar Flow Conditions, Experiments in Fluids,* 4, and McLaughlin, John B. 1993, *The Lift on a Small Sphere in a Wall-Bounded Linear Shear Flows, Journal of Fluid Mechanics,* 246.

The character of the shear flow depends on factors such as the character of the surface of the permeable membrane and the velocity of the fluid flow across the permeable membrane. As the velocity of the fluid flow increases, the shear rate increases. However, higher fluid flow velocities result in more turbulent fluid flow, whereas lower fluid flow velocities produce more laminar flow. To effect the desired motion of the substances in the fluid, high shear is preferably used; hence the present inventive methods and systems preferably involve turbulent fluid flow. The shear rates are preferably from about 10,000 sec$^{-1}$ to about 1,000,000 sec$^{-1}$ or more preferably from about 100,000 sec$^{-1}$ to about 500,000 sec$^{-1}$, although even higher shears are suitable for use in the inventive methods and systems.

FIG. 1 illustrates a velocity profile that occurs near a permeable membrane 10 in a tangential fluid flow, such as a flow of process fluid tangentially across the permeable membrane 10. The tangential fluid flow, indicated by arrows 12, is on the feed or upstream side of the permeable membrane 10. A fraction of the fluid flow permeates through the permeable membrane 10 to the permeate or downstream side of the permeable membrane 10. Although other situations are possible in various embodiments of the present invention, pressure on each side of the permeable membrane 10 is preferably uniform, with the greater pressure being on the upstream side, thereby contributing to the permeate flow.

When the tangential fluid flow is turbulent, three distinct flow regions are frequently discernible as illustrated in FIG. 1. The dimensions of these regions vary with the shear rate. The region nearest the upstream surface of the permeable membrane 10 is the viscous sublayer or, as it is often called, the laminar sublayer. The high shear rates preferably used in the present invention can produce viscous sublayers as thick as about 10 μm or more. In this region, turbulent fluctuations can be suppressed by the surface of the permeable membrane 10, especially a smooth surface permeable membrane 10 as discussed herein. In the viscous sublayer, shear stress is transmitted through the fluid almost exclusively by viscosity, and velocity can increase substantially linearly with distance from the surface of the permeable membrane 10.

The region farthest from the upstream surface of the permeable membrane 10 is the turbulent region. In this region, the shear stress is transmitted almost exclusively by the random fluctuating motion of the fluid (i.e., Reynolds stress). In this turbulent region, the average velocity is substantially uniform and independent of the distance from the permeable membrane 10 as illustrated in FIG. 1.

The region intermediate the viscous sublayer and the turbulent region is the inertial sublayer. The relatively high shear preferably used in the present invention produces an inertial sublayer from about 10 μm to about 500 μm thick. In this region, the shear stress can be transmitted partially by viscosity and partially by fluctuating transport of momentum. Viscosity dominates near the viscous sublayer, while fluctuating transport of momentum dominates near the turbulent region. In this inertial sublayer, the average velocity generally varies in logarithmic relationship to the distance from the upper surface of the permeable membrane 10.

As illustrated in FIG. 1, the velocity of the fluid can have an average part which varies linearly near the upstream surface of the permeable membrane 10, varies logarithmically farther away from the permeable membrane 10, and finally becomes uniform still farther from the permeable membrane 10. Superimposed on this average velocity in each region is a fluctuating velocity. Relatively little of this fluctuating motion occurs in the viscous sublayer due to the surface effect of the permeable membrane 10 discussed herein; more occurs in the inertial sublayer, and finally the motion of the fluid is dominated by the fluctuating velocity in the turbulent region. The fluctuating velocity in each region is illustrated in FIG. 2A by swirling arrows 16.

Because the membrane 10 is permeable, the permeate flow 12, illustrated in FIG. 1, convects velocity fluctuations 16 towards the upstream surface of the permeable membrane 10 as illustrated in FIG. 2B. If the permeate flow rate is high enough, the viscous sublayer can be substantially eliminated. Accordingly, the permeate flow rate is preferably controlled as explained herein so as to maximize the viscous sublayer.

Velocity fluctuations also can be increased in the viscous sublayer if the surface of the permeable membrane 10 is not smooth, as illustrated in FIG. 2C. Vortices can shed off of protrusions or regions of recirculation and can contribute to velocity fluctuations and diminish the role of the permeable membrane 10 in suppressing fluctuations. Accordingly, to maintain the integrity of the viscous sublayer, the upstream surface of the permeable membrane 10 preferably is smooth (e.g., having a surface roughness which is small compared to the thickness of the viscous sublayer).

Figure 3:
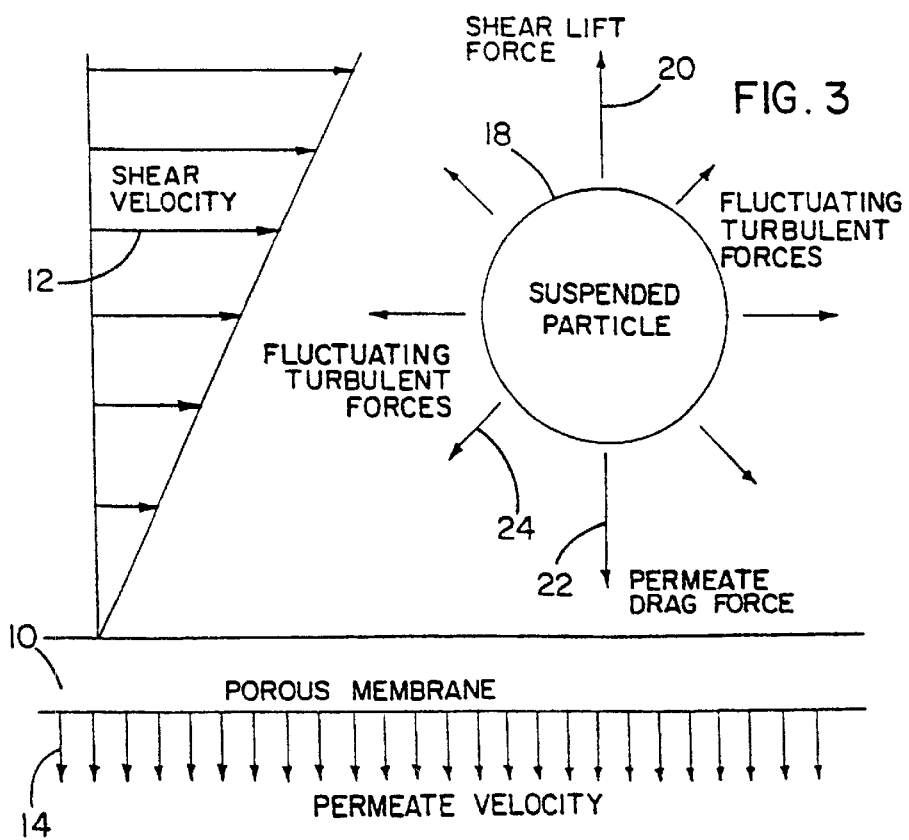
FIG. 3 is a diagrammatic representation of the forces acting on a particle suspended in process fluid subjected to the feed stream tangential flow across a permeable membrane and the permeate flow emerging from the permeable membrane.

A body or substance suspended in the process fluid near the surface of the permeable membrane also experiences a force (i.e., the permeate drag force) due to the permeate flow that tends to drive it toward the surface. When the substance is a macromolecule, to generate a lift force sufficient to balance the drag force of any useful permeate flow, the shear rate can be so large that turbulence becomes a dominant characteristic of the flow. However, as described herein, so long as the permeate rate is not too large, the effect of velocity fluctuations in the viscous sublayer is small, even if the turbulence is relatively strong in the turbulent region. As a model for the operation of the present invention, it can be assumed, as illustrated in FIG. 3, that in the viscous and inertial sublayers, the average velocity imposes a lift force on a substance 18, indicated by arrow 20, and a drag force, indicated by arrow 22, as if the turbulence were not present. In addition, the turbulence applies forces which fluctuate rapidly in both direction and magnitude. Because these fluctuations are both rapid and random, it can be assumed that the fluctuating forces have an average value of zero and have no effect other than to increase the apparent diffusion coefficient of the macromolecules in the fluid.

As described herein, essentially all of the shear stress is transmitted by viscosity in the viscous sublayer but only part of it is transmitted by viscosity in the inertial sublayer, the rest being transmitted by turbulent fluctuations. Because of this, the lift force applied to a substance in the viscous sublayer, substance 1 in FIG. 4 for example, can be substantially larger than that applied to a substance of the same size in the inertial sublayer, such as substance 2 in FIG. 4. This difference is far greater than would be accounted for in a laminar flow system by the difference in distance to the upstream surface of the permeable membrane from the locations of the two substances. To experience the large lift force generated in the viscous sublayer, the suspended substance, e.g., substance 1 in FIG. 4, is preferably completely immersed in that sublayer (i.e., substances are preferably smaller than the thickness of the viscous sublayer). Substances, e.g., substance 4, that are large compared to the thickness of the viscous sublayer can still be small enough to experience the lesser lift force of the inertial sublayer, which can be a few orders of magnitude thicker than the viscous sublayer in most turbulent flows. The lift force on a large substance, e.g., substance 3, which penetrates partially into the viscous sublayer but is so large that most of its surface is in the inertial sublayer cannot be as large as that on a small substance centered at the same location. From this a conclusion can be drawn that the large lift force due to the large shear rate in the viscous sublayer is available principally to substances that are small with respect to the thickness of that layer.

The permeate flow velocity is preferably small compared to the average tangential velocity in the fully turbulent region, e.g., less than one hundredth of the tangential velocity. In some embodiments, the permeate velocity is on the order of about 1/1000 of a m/sec. or less while the average tangential velocity is on the order of 10 m/sec or more. For example, for a 16P2 (16 inch or 40.64 cm rotor diameter) dynamic filtration machine manufactured by Pall Corporation, at 1800 rpm and 1000 lmh permeate rate, the average tangential velocity can be about 19 m/sec, and the permeate velocity can be about $3\times10^{-4}$ m/sec. In this case, the permeate flow rate exerts a negligible effect on the thickness of the viscous sublayer.

In operation of embodiments of the invention, a substance (e.g., a molecule of given size) can be separated or concentrated from a solution or suspension in which it is suspended by balancing the lift and drag forces exerted on it in the viscous sublayer by manipulating the shear rate and the permeate flow rate. For example, for a given size substance at a given shear rate in the viscous sublayer, an upper limit on the permeate flow rate can be selected such that the permeate drag (e.g., as calculated by the Stokes formula) is equal to the lift. If the permeate flow rate is increased above this point, the substance can be dragged through the permeable membrane. If the permeate flow rate is at or below this point, the substance can remain suspended on the upstream side near the surface of the permeable membrane by the shear lift. Alternatively, or in addition, for a given size substance at a given permeate flow rate, an upper limit on the shear rate in the viscous sublayer can be selected such that the shear lift is equal to the permeate drag. If the shear rate is decreased below this point, the substance can be dragged through the permeable membrane. If the shear rate is at or above this point, the substance can remain suspended on the upstream side near the surface of the permeable membrane.

The permeate flow establishes the drag force acting on substances upstream of the permeable membrane. In essence, the process fluid is drawn through the membrane (i.e., from the upstream side of the membrane to the downstream side) into the permeate, which generally includes substances smaller than the shear separation size. Any method of creating permeate flow can be employed in the context of the present invention. Generally, the permeate flow is established by creating a drop in pressure across the permeable membrane. The rate of permeate flow can be controlled in any number of ways, including, for example, by restricting the flow of permeate in the permeate outlet of a separation device. The characteristics of the permeable membrane can also be used to affect-the permeate flow rate (e.g., thickness, voids volume, etc.). In addition, any means of adjusting the transmembrane pressure can be used to control the permeate flow rate.

The shear lift is also created in proximity to the surface of the permeable membrane. Any method of creating shear within the process fluid can be employed in the context of the present invention. Typically, shear is established by effecting relative motion of the process fluid in a direction tangential to the surface of the permeable membrane. The shear then establishes the lift force acting on particles upstream of the permeable membrane. As discussed herein, the lift acting on some particles is sufficient to retain them upstream of the membrane, even in the presence of the permeate flow.

The shear separation size for a given protocol reflects the balance of the drag force and lift force acting on the particles upstream of the membrane. The opposition of these forces is illustrated in FIG. 3. In general, the drag force increases with increasing particle size and with increasing permeate flow rate. Accordingly, for a given size particle, the drag force can be varied by varying the permeate flow rate. The lift force which opposes the drag force increases with increasing particle size, with increasing shear rate, and with a decreasing distance from the permeable membrane. Accordingly, for a given size particle and a given distance from the permeable membrane, the lift force can be varied by varying the shear rate. The net force acting on the particle can be adjusted to any value by suitably balancing the shear rate and the permeate flow rate. Therefore, the balance of lift and drag forces retards the transmembrane passage of substances larger than the separation size yet allows substances smaller than the separation size to pass through the permeable membrane into the permeate. Utilizing the balance between lift force and drag force as the primary means for establishing separation size enhances the precision with which substances above and below the cutoff size can be separated. Thus, in some embodiments, microfiltration or ultrafiltration can be achieved with more sharply tuned size and/or molecular weight cutoff characteristics.

A membrane for use in the shear separation systems, methods, and devices can be of any type suitable for generating sufficient shear at the membrane surface, and suitable porous membranes are known in the art. The membrane can be fashioned from any suitable material (e.g., metal, ceramic, paper, polymer, etc.), so long as it is compatible with the process fluid to be treated. Moreover, the dimensions of the membrane can also vary considerably within the boundaries of compatibility with the inventive systems and methods. Thus, the membrane can be of any suitable size or thickness. Moreover, as the shear is primarily responsible for establishing the shear separation size, membranes for use in the present invention can have a wide variety of pore ratings or molecular weight cutoffs. However, as discussed herein, the surface of the membrane is preferably sufficiently smooth to establish a viscous sublayer adjacent to the surface. For the purpose of estimating the effect on the viscous sublayer, at least two measures of smoothness are appropriate for a permeable membrane. Both the pore size and the variation of the height of the surface of the membrane between the pores are preferably small compared to the thickness of the viscous sublayer. For the purpose of shear separation, a smooth membrane which does not significantly interfere with the formation of the viscous sublayer can be, for example, one for which the sum of the pore size and the root mean square variation of surface height is less than about one fifth of the thickness of the viscous sublayer.

Because the separation size is a function of the shear and permeate flow, the pore rating of the membrane (or molecular weight cutoff) is not directly related to resolution. The permeable membrane is utilized primarily as a surface adjacent to which the shear flow is generated. Thus, one advantage of the present inventive method and system is that separation sizes smaller than the pore rating of the membrane can be achieved, thereby minimizing membrane fouling increasing transmission, and prolonging the usable life of a separation system. This can also reduce the number of separation steps required, for example, in the method of isolating a single protein molecule from a cell lysate suspension or separating a protein from a milk product. A second advantage is that a broad range of separation cutoff sizes can be achieved with one membrane by varying the ratio of shear lift to permeate drag. This makes it possible to perform several separation steps of a separation method with a single permeable membrane simply by recycling the permeate of one step as the feed of the next step with the shear lift and permeate drag adjusted for a smaller or larger separation cutoff size. Therefore, the pore size or molecular weight cutoff of the membrane preferably is larger than the separation cutoff size, such as at least one and a half or at least twice the desired separation size (e.g., at least three times the separation size), and can be as much as at least five times the separation size (such as at least eight times the desired separation size) or even larger (e.g., at least ten times the desired separation size, or even up to about fifteen times the desired separation size or larger). Thus, for example, where the desired separation size is less than about 70 kD, a membrane with a pore rating of about 100 kD is suitable, although membranes with larger pores can also be employed. Moreover, where the desired separation size is about 100 kD to about 150 kD, a membrane with a pore rating of about 300 kD to about 500 kD is suitable. Alternatively, the separation medium can have a pore size or a molecular weight cutoff substantially equal to the desired separation cutoff size. In this embodiment, the permeable membrane also serves as a "last chance" filter. Of course, the pore rating of a membrane is preferably not smaller than the predetermined shear separation cutoff size. Generally, the pore rating of a membrane suitable for shear separation has a pore rating of less than about 1000 kD, as larger pores adversely impact the desired smoothness of the membrane surface. More preferably, the pore rating is about 500 kD or less (e.g., about 300 kD or less), or even about 100 kD or even smaller. However, a membrane having pores larger than even 1000 kD could be employed in the inventive shear separation methods and systems if the surface can be rendered sufficiently smooth to establish lift appropriate to balance the drag, as mentioned herein.

The inventive shear separation systems and methods provide means of treating any suitable fluids. For example, the invention shear separation systems and methods may be used to separate various proteins from a wide variety of protein-containing liquids, including blood or blood fractions and cell cultures or lysates of cell cultures, such as yeast, bacteria, plant and mamalian cell cultures.

A particular example is the treatment of milk products, particularly skim milk and whey products. The present invention is well suited to treat any type of milk product, especially skim milk and whey products. Skim milk is prepared by removing the cream from whole milk, and skim milk products include raw skim milk as well as fractions therefrom (e.g., milk or milk products which have been previously subjected to filtration or other separatory methods, including but not limited to whey and whey products). Whey typically is produced in cheese making, although the present invention is intended to encompass the use of other types of whey. Whey products include whey as well as fractions therefrom. As such, whey products include, for example, cheese whey, clarified whey, whey powder, pasteurized whey, whey concentrates, and other whey fractions (e.g., whey or whey products which have been previously subjected to filtration or other separatory methods).

If proteins are to be recovered from the milk product, it is desirable that the milk product not be heated to a temperature which could adversely affect the proteins therein (e.g., denature the proteins, particularly the immunoglobulins or recombinant proteins, therein). In particular, the milk product is desirably maintained at a temperature of about 60° C. or less, preferably at a temperature of about 50° C. or less, more preferably at a temperature of about 40° C. or less, and most preferably at about 20–25° C. or below. Thus, the milk product is preferably neither pasteurized nor derived from a pasteurized milk product. Preferably, the milk product, such as raw skim milk or whey, is obtained as a product from milk which has been subjected to filtration, such as in accordance with the inventive method or via dynamic filtration such as disclosed in U.S. Pat. Nos. 5,256,437, 5,356,651, and 5,401,523 to remove bacteria therefrom.

Thus, the present invention provides systems and methods of treating a milk product, particularly the bacteria-depleted and fat-depleted milk product (most particularly such a raw skim milk or whey-derived permeate), to concentrate a protein therein by treating the milk product via shear separation to form a protein-enriched retentate or a protein-enriched permeate (depending on the size of the protein relative to the separation size). Typically, a whey product contains many proteins of different molecular weights, particularly immunoglobulins, lactoferrin, lactoperoxidase, blood serum albumin, β-lactoglobulin, α-lactalbumin, and/or any recombinant proteins. Other milk products typically contain these same proteins, as well as casein. The present invention allows for the concentration of a particular protein or combination of proteins (e.g., first, second, third, fourth, and fifth (as well as any other) proteins) by the selection of particular shear separation conditions (e.g. the pore rating of the filtration medium, the drag force, and the lift force), and, alternatively, the use of a series of separation steps using different processing conditions (e.g., filtration media having increasingly smaller pore ratings, enhanced permeate flow, decreased lift, and even conventional separation techniques in conjunction with the present inventive method).

In the aforedescribed protein concentration method, the first, second, third, fourth, and fifth (as well as any other) proteins can be any suitable proteins. Desirably, proteins of higher molecular weight (MW) are concentrated before proteins of lower molecular weight. Typically, the proteins will be selected from the group consisting of immunoglobulins, lactoferrin, lactoperoxidase, blood serum albumin (usually bovine serum albumin when the ultimate source of the milk product is bovine milk), β-lactoglobulin, and α-lactalbumin. When the milk product contains all of these proteins, then, typically, the first protein will be immunoglobulins (generally about 150–900 kD MW); the second protein will be lactoferrin (generally about 74–90 kD MW) and lactoperoxidase (generally about 77.5 kD MW); the third protein will be blood serum albumin (generally about 66 kD MW); the fourth protein will be β-lactoglobulin (generally present in dimeric form of about 36 kD MW), and the fifth protein will be α-lactalbumin (generally about 14 kD MW). The present inventive systems and methods, of course, are applicable to other proteins, of larger or smaller molecular weight. Of course, where the milk product also contains a recombinant protein, its molecular weight generally will be known. Similarly, the present inventive systems and methods can be used to remove combinations of proteins based on the molecular weights of the proteins relative to the separation size of the separation protocol used. For example, instead of separately removing blood serum albumin and β-lactoglobulin from a milk product, these proteins can be separated together by a shear separation protocol creating drag sufficient to draw the albumin and β-lactoglobulin through the membrane, while creating lift sufficient to retain larger particles within the retentate. Of course, other combinations of proteins can be separated in a similar manner.

If the initial milk product is conventional raw skim milk or whey, then, after the aforesaid proteins are separated from the milk product, the resulting permeate will be fat- and protein-depleted and should contain only minerals, vitamins, and lactose. The removal and concentration of the various proteins can be accomplished in accordance with the present invention by, for example, subjecting the milk product permeate to the aforedescribed sequential shear separation protocols wherein (a) the first separation protocol effects a separation size of about 900 kD or more, preferably about 900–1,000 kD, to reject any residual fat and casein and to concentrate the proteins of interest in the permeate (although, as described herein, this step preferably is omitted in some embodiments of the present invention), (b) the second separation protocol effects a separation size of about 90 kD or more, preferably about 90–100 kD, to form an immunoglobulin-enriched retentate, (c) the third separation protocol effects a separation size of about 60–70 kD, preferably about 60–65 kD, to form a lactoferrin/lactoperoxidase-enriched retentate, (d) the fourth separation protocol effects a separation size of about 40–60 kD, preferably about 50–60 kD, to form a blood serum albumin-enriched retentate, (e) the fifth separation protocol effects a separation size of about 15–25 kD, preferably about 15–20 kD, to form a β-lactoglobulin-enriched retentate and an α-lactalbumin-enriched permeate, and/or (e) the sixth separation protocol effects a separation size of about 10 kD or less, preferably about 5–10 kD, to form a β-lactalbumin-enriched retentate and a substantially protein-depleted permeate containing smaller molecular weight components, such as peptides, minerals, vitamins, and lactose.

Any suitable device or system, such as a dynamic filtration assembly, can be used for the generation of the shear forces and the permeate flow. The dynamic filtration assembly can be of any suitable configuration and typically will include a housing containing a separation assembly having at least one separation medium (preferably containing a permeable membrane) and a mechanism to effect relative movement between the fluid being filtered and separation medium. The housing can include a process fluid inlet arranged to direct process fluid into the housing and a permeate outlet arranged to direct permeate from the housing. In addition, the housing also can include a retentate outlet arranged to direct retentate from the housing.

Where the separation medium includes a permeable membrane, the membrane typically has an upstream surface which communicates with the process fluid inlet and a downstream surface which communicates with the permeate outlet. Depending upon the desired shear separation protocol, the permeable membrane can have pores larger (even substantially larger, as described herein) than the size of substances to be retained upstream of the permeable membrane. Moreover, to maximize the depth of the viscous sublayer, the permeable membrane can additionally have a surface roughness which is small compared to a viscous sublayer thickness on at least its upstream surface, as described herein. To effect the shear separation as herein described, the mechanism to effect relative movement between the fluid being filtered and separation element generally is preferably a means for generating a shear adjacent to the upstream surface of the permeable membrane. Such means preferably establishes shear forces in the process fluid sufficient to retard the passage of substances to be retained upstream of the permeable membrane in the presence of a permeate flow. The shear forces thus generated are preferably sufficient to retard the passage of substances smaller than the viscous sublayer thickness through the permeable membrane in the presence of the permeate flow.

The separation assembly and the mechanism to effect relative movement between the fluid being filtered and separation medium can have any of a variety of suitable configurations. For example, the separation assembly can comprise stationary filter elements and rotating interleaved discs or rotating filter elements and stationary interleaved discs such as those disclosed in International Publication No. WO95/00231and International Publication No. WO96/01676. Alternatively, the separation assembly can comprise stationary filter elements and a rotatable housing such as those described in International Publication No. WO97/13571.

Process fluid which is to undergo shear separation can be supplied to a dynamic filtration assembly by any number of means, for example, by any of the means described in International Publication Nos. WO95/00231 and WO96/01676. The process fluid can be directed through the process fluid inlet into the housing, for example, at a predetermined pressure and flow rate. The process fluid then flows tangentially along the upstream surface of the permeable membrane and out of the housing through the retentate outlet. The transmembrane pressure forces permeate through the permeable membrane from the upstream surface to the downstream surface, and the permeate is removed from the housing via the permeate outlet.

As the process fluid is introduced into the housing of the dynamic filtration assembly, an angular momentum is imparted to the process fluid causing it to rotate at a particular velocity. The rotation of the fluid effects the shear described herein. The angular momentum can be imparted to the fluid in any number of ways. For example, as described in International Publication No. WO96/01676, relative rotation between the separation assembly and a separate member facing the separation medium can be produced, e.g., the member can be rotated or the separation medium can be rotated. Alternatively, as described in International Publication No. WO97/13571, the housing can be rotated. In both cases, the rotational movement transfers an angular momentum to the process fluid thereby creating a shear. As described herein, the shear generates lift on particles or substances in the process fluid while permeate flow generates drag on particles or substances in the process fluid. Both of these parameters can be adjusted to generally balance the lift and drag forces on a particle or substance at a predetermined separation size as described herein. For example, the shear rate can be adjusted by changing the revolution velocity, and the permeate flow can be adjusted by changing the transmembrane pressure.

A shear separation system embodying the invention may include a control system and a dynamic filtration assembly. As discussed above, a shear separation system may be used to separate particles or substances of varying size, even when a separation medium has a separation cutoff size greater than the size of the particles of interest. The effective separation cutoff size of a dynamic filter assembly depends principally on shear lift and permeate drag forces. More particularly, the effective separation cutoff size can be controlled by adjusting the relative magnitudes of shear lift and permeate drag forces. Accordingly, by utilizing a control system which senses the effective separation cutoff size and varies shear lift and/or permeate drag, the effective separation cutoff size of a dynamic filter assembly can be controlled according to the needs of a particular application.

Figure 5:
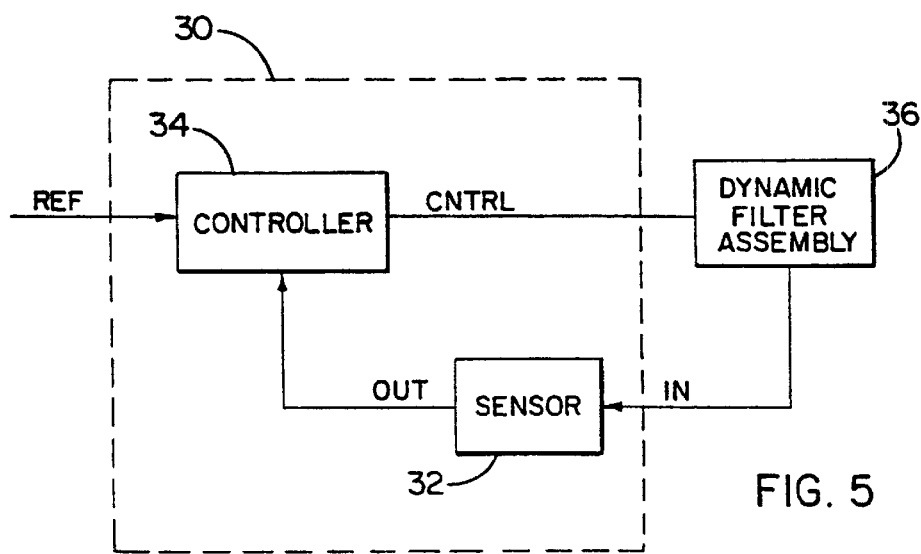
FIG. 5 is a diagrammatic representation of a shear separation system including a controller for controlling one or both of the shear lift and permeate drag forces.

An exemplary embodiment of a shear separation system including a control system 30 and a dynamic filter assembly 36 coupled to the control system 30 is illustrated in FIG. 5. The control system 30 comprises a sensor 32 and a controller 34 coupled to the sensor 32. Both the controller 34 and the sensor 32 may also be coupled to the shear separation device 36.

The dynamic filter assembly 36 comprises any device capable of separating particles of varying size using shear lift and permeate drag forces to effect separation. For example, the dynamic filter assembly 36 may create shear lift by rotating either a housing, one or more separation elements, or one or more disks or cylinders in contact with a process fluid. The shear separation system preferably also includes an arrangement of pumps, valves, and conduits to control fluid flow through the housing. For example, the dynamic filter assembly may include a housing suitable for containing the process fluid. One or more separation elements may divide the housing into a process fluid region and a permeate region. The housing may include a process fluid inlet to direct process fluid into the process fluid region of the housing and a retentate outlet to direct retentate fluid from the process fluid region of the housing. The housing may also include a permeate outlet to direct permeate fluid from the permeate region of the housing. A pump may be located upstream or downstream of the housing to control a fluid flow rate. The dynamic filter assembly may include a motor to generate shear lift by rotating the housing, the separation elements, and/or the disks or cylinders.

An exemplary dynamic filter assembly is disclosed in International Publication No. WO 97/13571, published on Apr. 17, 1997. However, the present invention is not limited to any particular type of dynamic filter assembly. Any device which effects separation using shear lift and permeate drag forces is within the scope of the invention.

The sensor 32 may comprise any type of sensor capable of being coupled to a dynamic filter assembly to measure the performance of the assembly. For example, the sensor 32 may comprise a particle size sensor which produces a signal, e.g., a current or a voltage, indicative of the size of one or more of the particles or substances in the permeate or the retentate and, therefore, indicative of the measured separation cutoff size of the dynamic filter assembly. In a preferred embodiment, the sensor 32 is coupled to a permeate conduit downstream of a separation medium in the dynamic filter assembly 36 to sense the size of particles or substances in the permeate and produce a signal indicative of the measured separation cutoff size of the device. Alternatively, the sensor 32 may be coupled to a retentate conduit on an upstream side of the separation medium to sense the size of particles in the retentate. A variety of suitable sensors 32, including counters or turbidity sensors, are readily available.

The controller 34 comprises any type of controller suitable for providing an output signal to vary shear lift and/or permeate drag in the dynamic filter assembly 36 based on one or more inputs. The controller 34 preferably receives a plurality of input signals and produces at least one output signal. In the illustrated embodiment, the controller 34 may receive a reference input signal indicative of a desired separation cutoff size and another input signal indicative of a measured or sensed separation cutoff size, e.g., the output from the sensor 32. The controller 34 preferably produces an error signal indicative of the difference between the reference input signal and the output from the sensor 32, and the error signal may comprise the output signal of the controller 34. In a preferred embodiment, the controller 34 processes the error signal into a format suitable for controlling operating parameters, e.g., parameters, such as rotational velocity and/or transmembrane pressure, which affect shear lift and/or permeate drag, in the dynamic filter assembly 36.

The controller 34 may be analog or digital and may include appropriate conditioning circuitry to condition the input signals. For example, if the inputs are analog signals, and the controller 34 is digital, the controller 34 may include an analog-to-digital (A/D) converter to convert the input signals into digital format for further processing. The controller 34 may also include a processing circuit, e.g. a microprocessor, which implements a control law and outputs a control signal to the dynamic filter assembly 36. The controller 34 may also include a digital-to-analog (D/A) converter to convert the control signal into an analog format for use in an analog device, e.g., the motor which drives the housing, filter elements, or disks of the dynamic filter assembly 36. In a preferred embodiment, the controller comprises a programmable logic controller (PLC).

In operation, a process fluid flow is established through the dynamic filter assembly 36, creating a transmembrane pressure across the separation medium in the device. The transmembrane pressure creates a permeate fluid flow which, in turn, creates a permeate drag force on particles in the process fluid on an upstream side of the separation medium. A shear lift force is produced on particles in the fluid on the upstream side of the separation medium, for example, by actuating a motor to rotate the housing, the filter elements, or the disks or cylinders in contact wit the process fluid. The shear lift force opposes the permeate drag force on the particles on the upstream side of the separation medium. By adjusting parameters affecting one or both of these forces, substances of a first size may remain on the upstream side of a separation medium and substances of a second size may pass through the separation medium to the downstream side. In a preferred embodiment, the sensor 32 senses the size of substances in the permeate or retentate and produces an output signal indicative of the measured separation cutoff size of the dynamic filter assembly 36.

The controller 34 receives one or more output signals from the sensor 32 and also receives one or more reference input signals indicative of a desired system output, e.g., a desired separation cutoff size for the dynamic filter assembly 36. In response, the controller 34 outputs one or more control signals to the dynamic filter assembly 36. For example, if the relationship between the sensor output and the reference input is within a predetermined tolerance, indicating, for example, that the measured separation cutoff size is equal or sufficiently close to the desired separation cutoff size, the controller 34 may output a control signal which does not significantly affect the operation of the dynamic filter assembly 36 because the assembly is operating as desired. If the relationship between the sensor output and the reference input is outside the predetermined tolerance, the controller 34 may output a control signal which affects the generation of dynamic filter assembly 36 in a manner which forces the relationship back within the predetermined tolerance. The controller 34 may increase or decrease the shear lift on the substances in the process fluid; the controller 34 may increase or decrease the permeate drag on the substances in the process fluid; or the controller 34 may increase or decrease both the shear lift and the permeate drag on the substances.

The mechanism by which the controller 34 causes the dynamic filter assembly 36 to adjust the shear lift and/or permeate drag depends on the type of dynamic filter assembly 36 being used to effect shear separation. For example, if the dynamic filter assembly utilizes relative rotation between the process fluid and the separation elements to create shear lift, the controller 34 may vary the speed of the motor which causes the rotation, thereby increasing or decreasing the shear lift. Alternatively, or additionally, the controller 34 may control one or more pumps to adjust the pressure differential across the separation elements in the dynamic filter assembly to increase or decrease the permeate flow rate and thereby adjust the permeate drag. The present invention is not limited to any particular mechanism for adjusting shear lift and/or permeate drag. Any method for controlling the relative magnitudes of shear lift and permeate drag are within the scope of the invention.

Although the illustrated embodiment depicts a single sensor 32, a single controller 34, and a single feedback loop, the present invention is not limited to such an embodiment. A control system may include a plurality of sensors which sense a plurality of outputs from a separation device. For example, sensors which sense the speed and/or acceleration of the motor may be included in addition to sensors which sense the size of the particles. Thus, the controller 34 may receive inputs from a plurality of sensors, implement a plurality of control laws and output a plurality of control signals to the dynamic filter assembly.

A shear separation method and system of the present invention can be used in a single pass mode or in a recirculation mode. For example, the retentate drawn through the retentate outlet can be redirected to the process fluid inlet for additional separation. Alternatively or in addition to the recirculation of the retentate, the permeate can be recirculated by drawing the permeate from the permeate outlet and into the process fluid inlet.

In addition to complete separation or substantially complete separation, the shear separation systems and methods of the present invention may also be utilized for concentration of the substances having a size less than the separation cutoff size and/or the substances having a size greater than the separation cutoff size. For example, substances having a size less than the predetermined separation cutoff size can pass through the permeable membrane in the permeate flow, resulting in a higher concentration of those substances on the downstream side of the permeable membrane than on the upstream side. Similarly, substances having a size greater than the predetermined separation cutoff size can be retained along the upstream side of the permeable membrane, resulting in a higher concentration of those substances on the upstream side of the permeable membrane than on the downstream side. Accordingly, the permeate can comprise a higher concentration of substances less than the predetermined separation cutoff size and the retentate can comprise a higher concentration of substances greater than the predetermined separation cutoff size.

EXAMPLES

The following examples further illustrate the present invention. In particular, they demonstrate that the inventive shear separation systems and methods can effect a separation size substantially smaller than the pore rating of any separation medium employed. The examples therefore demonstrate that the balance of shear lift and permeate drag forces can achieve separation of particles from a solution or suspension substantially independently of the size exclusion of the membrane. The examples further demonstrate that the inventive shear separation method can be employed to recover proteins from milk products. Of course, as these examples are included for illustrative purposes, they should not in any way be construed as limiting the scope of the present invention.

Example 1

This example demonstrates that the balance of shear lift and permeate drag forces can achieve separation of particles from a solution or suspension regardless of the size exclusion of the membrane.

In this example, the process fluid comprised a phosphate buffered saline solution (120 mM NaCl, 2.7 mM KCl, 10 mM phosphate buffer) with a 0.1% concentration of Bovine Serum Albumin (BSA), which is approximately 60 kD in size, and a 0.02% concentration of Lysozyme, which is approximately 16 kD in size. High Pressure Liquid Chromatography (HPLC) was used to determine the protein concentrations during the experiment. The tests were conducted at several spin rates (different shear rates) and permeate flow rates. A polyethersulfone membrane available from Pall Corporation under the trade designation FILTRON OMEGA UF was used in two different pore sizes in a Pall Corporation LAB6 dynamic filtration device. One pore size was such as to exclude proteins larger than 300 kD, and the other was such as to exclude proteins larger than 70 kD.

Figure 6A:
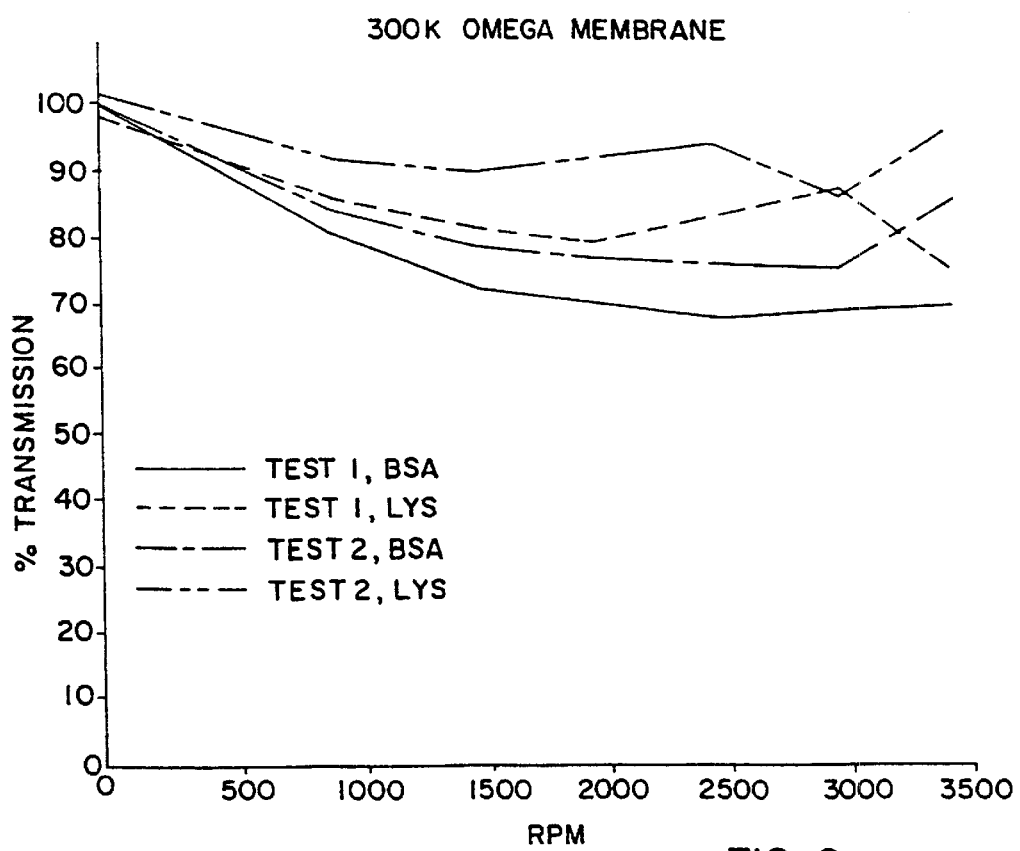
FIGS. 6A and 6B are graphical representations of the experimental results of protein separation using a shear separation method of the present invention in conjunction with 300 kD (FIG. 6A) and 70 kD (FIG. 6B) membranes.

FIG. 6A is a graph illustrating the results of two tests (test 1 and test 2) utilizing the 300 kD Filtron Omega UF membrane. The permeate duct of the grid on which the membrane was supported was restricted so that a permeate flow rate of approximately 30 ml/min was obtained. The retentate flow rate was about 1 l/min. For both tests, permeate was collected first at 3450 rpm, then at 3000, 2500, 2000, 1500, and 900 rpm in that order. These spin rates produce shear at the membrane surface of $5\times10^5$ sec$^{-1}$, $3\times10^5$ sec$^{-1}$, $2.5\times10^5$ sec$^{-1}$, $1.75\times10^5$ sec$^{-1}$, $1.0\times10^5$ sec$^{-1}$, and $4\times10^4$ sec$^{-1}$, respectively. A second sample was then collected at a spin rate of 3450 rpm. In the second test (test 2), an additional sample was taken at 2000 rpm with the retentate rate reduced to 0.5 l/min. At the end of the first test, a portion of the membrane, approximately 0.5 cm across, was found to have been torn off the support material. However, a dye test of the membrane had shown good uniformity of protein deposit over the grooves, which indicates reasonably uniform flow in spite of the tear. In the second test, the membrane was in good condition at the end of the experiment.

The pore structure of the 300 kD membrane is much too large to restrict transmission of either BSA or Lysozyme. This is shown in FIG. 6A by the 100% transmission of these two proteins at zero spin rate. Up to 1500 rpm, there is a distinct reduction in protein transmission through the membrane with increasing spin rate, with the heavier BSA being more strongly affected than the Lysozyme in each test. At higher spin rates, there is an indication that transmission can increase with spin rates. This is possibly a result of reducing the viscous sublayer thickness to the point that the surface roughness of the 300 kD media is sufficient to disrupt the viscous sublayer. The shift in the second 3450 point can be due to fouling of the membrane, or it can simply be an indication of scatter in the data. The shift in the second 2000 rpm point could be for the same reason. It is not large enough to conclude that it is due to retentate flow rate reduction. These experiments demonstrate the separation of proteins of two distinct sizes by a balance of shear lift and permeate drag forces alone, i.e., without any reliance on the size exclusion of the membrane.

Figure 6B:
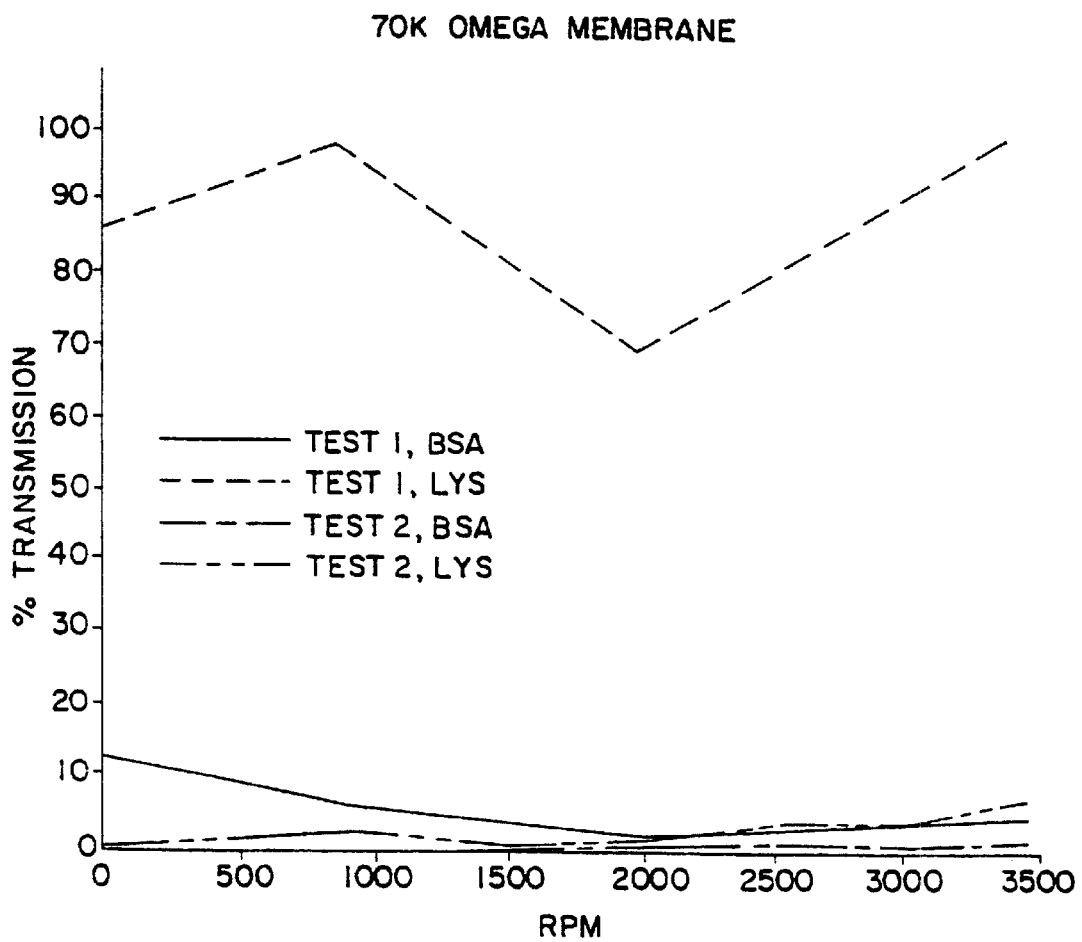

FIG. 6B is a graph illustrating the results of the tests (test 1 and test 2) utilizing the 70 kD Filtron Omega UF membrane. The second test utilizing the 70 kD membrane was conducted in the same manner as the two experiments with the 300 kD membranes except that the permeate flow rate was 18 ml/min, and the reduced retentate point at 2000 rpm was not tested. In the first test, the permeate rate was set at 160 ml/min, and a new membrane was used for each data point.

As illustrated in the graph, transmission of BSA through the 70 kD membrane is highly restricted, so interpretation of this graph is complicated by the likelihood of a BSA gel layer on the membrane. It is suspected that the 160 ml/min permeate flow rate is a large enough permeate rate to drag most of the Lysozyme through the shear layer at all spin rates, while 18 ml/min is so slow that the Lysozyme cannot penetrate the BSA gel layer. These last two tests demonstrate the use of shear forces balanced against drag forces to separate small proteins while large proteins are excluded by conventional filtration.

Example 2

This example demonstrates that the inventive shear separation method can produce an effective separation size substantially smaller than the pore rating of the filter medium employed.

In particular, an attempt was made to separate proteins from a suspension of lysed *E. coli* cells in PBS using an experimental polyethersulfone membrane from Pall Corporation called PV-20. The PV-20 is a double skinned polyethersulfone membrane that rates as an approximately 100 kD molecular weight cutoff. Electrophoresis gels of the permeate were used to determine protein concentration. In the experiment, permeate flow was set to 13 ml/min, and a rotation rate of 1935 rpm was used which produces a shear rate at the membrane surface on the order of $10^5$ sec$^{-1}$. The table below summarizes the results of the experiment.

| Protein Size (kD) | Concentration Ratio at 1935 rpm | Concentration Ratio at 0 rpm |
|---|---|---|
| 170 | 0.00% | 0.00% |
| 119 | 0.00% | 54.83% |
| 95/86 (two bands) | 0.00% | 70.55% |
| 41 | 16.74% | 96.91% |
| 27 | 37.02% | 105.57% |

As indicated by the results in the table, the transmission of proteins was significantly impeded by the shear even though the pores of the membrane were large enough to allow transmission of much larger molecules.

Example 3

This example illustrates how the shear separation method can be employed to recover the proteins from milk.

Whole milk is subjected to centrifugal separation or dynamic filtration (using a filtration medium having a pore rating of 0.8 μm) to produce a cream retentate and a skim milk permeate. The skim milk permeate is dynamically filtered (using a filtration medium having a pore rating of 0.4 μm) to produce a fat-enriched retentate and a fat/bacteria-depleted permeate.

The fat/bacteria-depleted permeate is subjected to shear separation using a filtration medium having a pore rating of 0.3 μm to generate an effective separation size of 0.05–0.2 μm to produce a micellar casein-enriched retentate (having a 15–20% total solids concentration, with a 60–70% micellar casein concentration of the total solids) and a milk serum permeate.

The milk serum permeate is subjected to a shear separation step using a filtration medium having a molecular weight cutoff of 500 kD to generate an effective separation size of 100 kD to produce an immunoglobulin-enriched retentate and an immunoglobulin-depleted milk serum permeate. The immunoglobulin-depleted milk serum permeate is subjected to shear separation using a filtration medium having a molecular weight cutoff of 200 kD to generate an effective separation size of 70 kD to produce a lactoferrin/lactoperoxidase-enriched retentate and a lactoferrin/lactoperoxidase-depleted milk serum permeate. The lactoferrin/lactoperoxidase-depleted milk serum permeate is recirculated through the filter and subjected to shear separation under conditions of decreased lift and/or increased drag to generate an effective separation size of 50 kD to produce a bovine serum albumin-enriched retentate and an immunoglobulin/lactoferrin/lactoperoxidase/bovine serum albumin-depleted permeate. Alternatively, the initial milk serum permeate can be subjected to an initial shear separation protocol using a filtration medium having a molecular weight cutoff of 200 kD with a suitable lift/drag ratio to generate an effective separation size of 50 kD to produce an immunoglobulin/lactoferrin/lactoperoxidase/bovine serum albumin-depleted permeate.

The immunoglobulin/lactoferrin/lactoperoxidase/bovine serum albumin-depleted permeate is recirculated through a 100 kD filter and subjected again to shear separation under conditions of decreased lift and/or increased permeate flow to generate an effective separation size of 20 kD to produce a β-lactoglobulin-enriched retentate and a β-lactoglobulin-depleted permeate. The β-lactoglobulin-depleted permeate is recirculated through the same filter and subjected again to shear separation under conditions of decreased lift and/or increased permeate flow to generate an effective separation size of 10 kD to produce an α-lactalbumin-enriched retentate and an α-lactalbumin-depleted permeate (containing non-fat, non-protein milk solids).

Example 4

This example illustrates how the shear separation method can be employed to recover the proteins from whey.

Cheese whey is subjected to centrifugal separation or dynamic filtration (employing a shear separation protocol generating an effective separation size of 0.65 μm) to produce a whey cream retentate and a fat-depleted whey permeate. The fat-depleted whey permeate is dynamically filtered (using a filtration medium having a pore rating of 0.4 μm) to produce a fat-enriched retentate and a fat/bacteria-depleted, protein-enriched permeate. The fat/bacteria-depleted, protein-enriched permeate is dynamically filtered (using a filtration medium having a pore rating of 0.2 μm) to produce fat/bacteria-enriched sludge retentate and a whey protein-enriched permeate.

The whey protein-enriched permeate is subjected to a shear separation step using a filtration medium having a molecular weight cutoff of 500 kD to generate an effective separation size of 100 kD to produce an immunoglobulin-enriched retentate and an immunoglobulin-depleted whey product permeate. The immunoglobulin-depleted whey product permeate is subjected to shear separation using a filtration medium having a molecular weight cutoff of 200 kD to generate an effective separation size of 70 kD to produce a lactoferrin/lactoperoxidase-enriched retentate and a lactoferrin/lactoperoxidase-depleted whey product permeate. The lactoferrin/lactoperoxidase-depleted whey product permeate is recirculated through the filter and subjected to shear separation under conditions of decreased lift and/or increased drag to generate an effective separation size of 50 kD to produce a bovine serum albumin-enriched retentate and an immunoglobulin/lactoferrin/lactoperoxidase/bovine serum albumin-depleted permeate. Alternatively, the initial whey product permeate can be subjected to an initial shear separation protocol using a filtration medium having a molecular weight cutoff of 200 kD with a suitable lift/drag ratio to generate an effective separation size of 50 kD to produce an immunoglobulin/lactoferrin/lactoperoxidase/bovine serum albumin-depleted permeate.

The immunoglobulin/lactoferrin/lactoperoxidase/bovine serum albumin-depleted permeate is recirculated through a 100 kD filter and subjected again to shear separation under conditions of decreased lift and/or increased permeate flow to generate an effective separation size of 20 kD to produce a β-lactoglobulin-enriched retentate and a β-lactoglobulin-depleted permeate. The β-lactoglobulin-depleted permeate is recirculated through the same filter and subjected again to shear separation under conditions of decreased lift and/or increased permeate flow to generate an effective separation size of 10 kD to produce an α-lactalbumin-enriched retentate and an α-lactalbumin-depleted permeate (containing non-fat, non-protein milk solids).

Example 5

This example demonstrates the concentration of a recombinant protein from the milk of a transgenic mammal. In particular, a single filter is employed to separate a recombinant (α-antitrypsin (αAT), a protein of about 51 kD, from the milk. See Archibald et al, *Proc. Nat. Acad. Sci. USA*, 87(13), 5178–82 (1990).

Raw milk containing αAT obtained from a transgenic mammal is first processed to produce a milk serum (i.e., milk substantially free of fat, bacteria, and micellar casein). The milk serum containing the αAT is dynamically filtered in accordance with the present invention using a membrane with a molecular weight cutoff of about 100 kD. The first filtration step employs conditions of suitably high shear rate and low permeate rate to draw most of the particles smaller than αAT (e.g., the first permeate comprises β-lactoglobulin (about 35 kD in dimeric form) and α-lactalbumin (about 15 kD)) through the membrane while retaining αAT and larger particles in the retentate upstream of the membrane. The permeate is collected in a permeate collection chamber, and the retentate is collected in a retentate collection chamber. Thereafter, the retentate is again dynamically filtered in accordance with the present inventive method using the same membrane. The lift on the particles during the second filtration is suitably reduced (e.g., by slightly reducing the shear rate and/or increasing the permeate rate) so as to draw most of the αAT through the membrane yet maintained suitably high enough to retain particles larger than the αAT (e.g., immunoglobulins (about 150–900 kD), lactoferrin and lactoperoxidase (each about 75 kD), and blood serum albumin (about 60 kD)) in the retentate upstream of the membrane. The second permeate contains a substantially greater concentration of αAT and a substantially reduced concentration of other milk components than the initial process fluid, and is collected in a permeate collection chamber other than that containing the first permeate.

Example 6

This example demonstrates that a smooth filter medium creates a stronger, less turbulent shear boundary layer for filtration (allowing for a longer filtration life). In particular, the effect of placing the smooth side (i.e., the cast side) of an unsupported membrane facing upstream in contact with the process fluid, was evaluated as compared to placing the rough side (i.e., the side opposite the cast side) of the same unsupported membrane facing upstream in contact with the process fluid.

Each of two unsupported, 0.8 μm pore rated, nylon membranes from the same batch or roll of nylon membrane was mounted in a Pall Corporation LAB6 dynamic filtration machine, with the only difference being the orientation of the membrane, namely either smooth or rough side facing upstream. Each of these filtration machines was fed milk from a common feed tank and a common pump. A flow decay test was run on both machines in parallel. In this test, the permeate rate was brought up to 400 ml/min, and the spin rate was brought up to 2100 rpm during a short start up period. The feed pressure and valve settings were maintained approximately constant on both machines, and the permeate flow was allowed to decay by whatever fouling occurred. The table below summarizes the results of the experiment.

| Time (minutes) | Smooth Side Upstream-Permeate Flow (ml/min) | Rough Side Upstream-Permeate Flow (ml/min) |
| --- | --- | --- |
| 2 | 0 | 0 |
| 6 | 128 | 130 |
| 10 |  | 400 |
| 12 | 394 |  |
| 15 |  | 404 |
| 16 | 420 |  |
| 30 | 413 | 373 |
| 47 | 388 |  |
| 48 |  | 293 |
| 58 | 380 | 241 |
| 67 |  | 209 |
| 68 | 374 |  |
| 73 | 380 | 182 |
| 90 | 362 | 146 |
| 105 | 351 | 112 |
| 120 | 348 | 86 |
| 135 | 323 | 60 |
| 150 | 315 | 46 |
| 165 | 310 | 38 |
| 180 | 302 | 28 |
| 195 | 300 | 26 |
| 210 | 286 | 20 |
| 225 | 287 | 18 |
| 240 | 278 | 18 |
| 250 | 260 | 14 |

As indicated by the results in the table, the permeate flow decayed much more significantly and quickly when the rough side of the membrane was facing upstream than when the smooth side of the membrane was facing upstream. In particular, within 58 min (about 1 hr), the permeate flow was only 60% of the maximum observed permeate flow in connection with the rough side of the membrane facing upstream, as compared with a permeate flow of 90% of the maximum observed permeate flow in connection with the smooth side of the membrane facing upstream. Similarly, after 2 hr, 3 hr, and 4 hr, the permeate flow decreased to 21%, 7%, and 4% of the maximum observed permeate flow, respectively, in connection with the rough side of the membrane facing upstream, as compared with permeate flows of 83%, 72%, and 66%, of the maximum observed permeate flow, respectively, in connection with the smooth side of the membrane facing upstream. These data demonstrate that a smooth filter medium promotes a stronger, less turbulent shear boundary layer for filtration.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of treating a process fluid to concentrate or separate substances having a size less than a predetermined separation size and substances having a size greater than the predetermined separation size comprising:
   generating a permeate flow through a permeable membrane including establishing permeate drag forces;
   creating a turbulent flow of process fluid across a permeable membrane including generating a shear flow having a shear rate of about 100,000 sec$^{-1}$ or more at the surface of the permeable membrane and establishing shear lift forces; and
   balancing the permeate drag forces and shear lift forces to retard passage through the permeable membrane of substances having a size greater than the predetermined separation size and to allow passage through the permeable membrane of substances having a size less than the predetermined separation size.

2. The method of claim 1, wherein generating a permeate flow through a permeable membrane includes generating a permeate flow through a permeable membrane having a pore size or molecular weight cutoff which is larger than said separation size.

3. The method of claim 2, wherein said pore size or molecular weight cutoff of said membrane is at least twice said separation size.

4. The method of claim 3, wherein said pore size or molecular weight cutoff of said membrane is at least three times said separation size.

5. The method of claim 4, wherein said pore size or molecular weight cutoff of said membrane is at least five times said separation size.

6. The method of claim 5, wherein said pore size or molecular weight cutoff of said membrane is at least eight times said separation size.

7. The method of claim 1, wherein generating a shear flow includes establishing a viscous sublayer adjacent to an upstream surface of said permeable membrane.

8. The method of claim 7, wherein generating a shear flow retards the passage of particles smaller than the viscous sublayer thickness through the permeable membrane.

9. The method of claim 7, wherein said membrane has a surface roughness small compared to the thickness of said viscous sublayer.

10. The method of claim 1, wherein said process fluid is derived from milk.

11. The method of claim 1, wherein said substance includes a protein.

12. The method of claim 11, wherein said protein includes a recombinant human protein.

13. The method of claim 11, wherein said protein includes an immunoglobulin.

14. The method of claim 1, wherein creating the shear flow includes flowing the process fluid across the surface of the permeable membrane.

15. The method of claim 14 wherein balancing the permeate drag forces and shear lift forces includes adjusting the flow rate of process fluid across the permeable membrane.

16. The method of claim 1, wherein creating the shear flow includes relatively rotating the permeable membrane and the process fluid.

17. The method of claim 1, wherein said separation size is less than about 150 kD.

18. The method of claim 17, wherein said separation size is less than about 70 kD.

19. The method of claim 18, wherein said separation size is less than about 25 kD.

20. The method of claim 17, wherein said separation size is less than about 10 kD.

21. The method of claim 1 wherein generating a permeate flow through a permeable membrane and creating a turbulent flow of process fluid across a permeable membrane include establishing a permeate flow velocity which is less than about one hundredth of the tangential flow velocity.

22. The method of claim 1 wherein generating a permeate flow through a permeable membrane includes generating a permeate flow through a permeable membrane having a pore size of about 1000 kD or less.

23. The method of claim 22 wherein generating a permeate flow through a permeable membrane includes generating a permeate flow through a permeable membrane having a pore size of about 500 kD or less.

24. A shear separation method comprising:
generating a permeate flow through a permeable membrane having a pore size or molecular weight cutoff substantially larger than a predetermined separation size and establishing permeate drag forces;
creating a turbulent flow of a process fluid adjacent a permeable membrane including generating a shear flow having a shear rate of about 100,000 sec$^{-1}$ or more including establishing shear lift forces; and
balancing the permeate drag forces and shear lift forces to retard the passage of substances to be retained on the upstream surface of the permeable membrane.

25. The method of claim 24, wherein balancing the permeate drag forces and shear lift forces comprises adjusting at least one of the permeate flow and shear flow.

26. The method of claim 24, wherein creating a shear flow includes flowing the process fluid across the upstream surface of the permeable membrane.

27. The method of claim 26 wherein balancing the permeate drag forces and shear lift forces includes adjusting the process fluid flow rate across the permeable membrane.

28. The method of claim 24, wherein creating shear flow includes relatively rotating the permeable membrane and the process fluid.

29. The method of claim 24, wherein said permeable membrane has a surface roughness less than about one fifth the thickness of the viscous sublayer.

30. The method of claim 24 wherein said predetermined separation size is less than about 150 kD.

31. The method of claim 30 wherein said predetermined separation size is less than about 70 kD.

32. The method of claim 31 wherein said predetermined separation size is less than about 25 kD.

33. The method of claim 32 wherein said predetermined separation size is less than about 10 kD.

34. The method of claim 24 wherein generating a permeate flow through a permeable membrane and creating a turbulent flow of process fluid adjacent a permeable membrane include establishing a permeate flow velocity which is less than about one hundredth of the tangential flow velocity.

35. The method of claim 24 wherein said substances include a macromolecule.

36. The method of claim 35 wherein said macromolecule includes a protein.

37. A shear separation method comprising:
generating a permeate flow through a smooth permeable membrane and establishing permeate drag forces;
creating a turbulent flow of a process fluid across a permeable membrane having a shear rate of about 100,000 sec$^{-1}$ or more including generating a shear flow boundary layer having a viscous sublayer adjacent to the upstream surface of the permeable membrane, and establishing shear lift forces; and
balancing the permeate drag forces and shear lift forces to retard the passage of particles smaller than the viscous sublayer thickness rough the permeable membrane.

38. The method of claim 37, wherein creating a shear flow includes establishing a viscous sublayer adjacent to the upstream surface of the permeable membrane and generating a permeate flow through a smooth permeable membrane includes generating a permeate flow through a smooth permeable membrane having a pore size or molecular weight cutoff which is larger than the viscous sublayer thickness.

39. The method of claim 37, wherein balancing the permeate drag forces and shear lift forces comprises adjusting at least one of the permeate flow and shear flow.

40. The method of claim 39, wherein creating a shear flow boundary layer includes flowing the process fluid across the upstream surface of the permeable membrane and adjusting at least one of the permeate flow and shear flow includes adjusting the flow rate of process fluid across the permeable membrane.

41. The method of claim 39, wherein creating a shear flow boundary layer includes relatively rotating the process fluid and the permeable membrane and wherein adjusting at least one of the permeate flow and shear flow includes adjusting the relative rotation of the permeable membrane and the process fluid.

42. The method of claim 37 wherein generating a permeate flow through a permeable membrane and creating a turbulent flow of process fluid across a permeable membrane include establishing a permeate flow velocity which is less than about one hundredth of the tangential flow velocity.

43. The method of claim 37 wherein generating a permeate flow through a smooth permeable membrane includes generating a permeate flow through a smooth permeable membrane having a pore size of about 1000 kD or less.

44. The method of claim 43 wherein generating a permeate flow through a smooth permeable membrane includes generating a permeate flow through a smooth permeable membrane having a pore size of about 500 kD or less.

45. The method of claim 37 wherein said particles include a macromolecule.

46. The method of claim 45 wherein said macromolecule includes a protein.

47. A method of concentration comprising:
generating a permeate flow through a permeable membrane from an upstream surface to a downstream surface and establishing permeate drag forces;
creating a turbulent flow of a process fluid adjacent a permeable membrane including generating a shear flow having a shear rate of about 100,000 sec$^{-1}$ or more at the surface and establishng shear lift forces; and
balancing the permeate drag forces and shear lift forces to retard the passage through the permeable membrane of substances having a size greater than a predetermined separation size and to allow passage through the permeable membrane of substances having a size less than the predetermined separation size, thereby concentrating at least one of:
(i) the substances having a size greater than the predetermined separation size at the upstream surface of the permeable membrane, and
(ii) the substances having a size less than the predetermined separation size at the downstream surface of the permeable membrane.

48. The method of claim 47, wherein generating a permeate flow through a permeable membrane includes generating a permeate flow through a permeable membrane having a pore size or molecular weight cutoff which is larger than the predetermined separation size.

49. The method of claim 47, wherein creating a shear flow includes flowing the process fluid across the upstream surface of the permeable membrane.

50. The method of claim 47, wherein creating a shear flow includes relatively rotating the permeable membrane and the process fluid.

51. The method of claim 47, wherein creating a shear flow includes establishing a viscous sublayer adjacent to the upstream surface of the permeable membrane and balancing the permeate drag forces and shear lift forces comprises adjusting at least one of the permeate flow and shear flow.

52. The method of claim 47 wherein generating a permeate flow through a permeable membrane and creating a turbulent flow of process fluid adjacent a permeable membrane include establishing a permeate flow velocity which is less than about one hundredth of the tangential flow velocity.

53. The method of claim 47 wherein generating a permeate flow though a permeable membrane includes generating a permeate flow through a permeable membrane having a pore size of about 1000 kD or less.

54. The method of claim 53 wherein generating a permeate flow through a permeable membrane includes generating a permeate flow through a permeable membrane having a pore size of about 500 kD or less.

55. The method of claim 47 wherein said substances include a macromolecule.

56. The method of claim 55 wherein said macromolecule includes a protein.

57. The method of claim 56 wherein said predetermined separation size is less than about 150 kD.

58. The method of claim 57 wherein said predetermined separation size is less than about 70 kD.

59. The method of claim 58 wherein said predetermined separation size is less than about 25 kD.

60. The method of claim 59 wherein said predetermined separation size is less than about 10 kD.

61. A shear separation system for treating a process fluid to concentrate or separate substances having a size less than a predetermined separation size and substances having a size greater than the predetermined separation size comprising:
 a housing;
 a process fluid inlet arranged to direct process fluid into the housing;
 a permeate outlet arranged to direct permeate from the housing;
 at least one separation element disposed within the housing and including a permeable membrane having a downstream surface which communicates with the permeate outlet, to establish a permeate flow through the permeable membrane and generate permeate drag forces at the upstream surface of the permeable membrane; and
 the separation element and the process fluid being arranged to create a turbulent flow of process fluid adjacent to the permeable membrane including generating a shear flow having a shear rate of about 100,000 sec$^{-1}$ or more and establishing shear lift forces in the process fluid to balance the permeate drag forces and retard the passage of the substances to be retained upstream of the permeable membrane.

62. The shear separation system of claim 61 further comprising a controller to adjust at least one of the shear lift forces and permeate drag forces and control the predetermined separation size.

63. The shear separation system of claim 61, wherein generating a shear flow includes establishing a viscous sublayer adjacent to the upstream surface of the permeable membrane and wherein the permeable membrane has a pore size or molecular weight cutoff which is larger than the viscous sublayer thickness.

64. The shear separation system of claim 61, wherein the separation element and process fluid being arranged to create a turbulent flow of process fluid comprises arranging the separation element and process fluid to rotate relative to one another.

65. The shear separation system of claim 64, wherein the separation element and process fluid being arranged to rotate relative to one another comprises arranging the separation element to rotate relative to the housing.

66. The shear separation system of claim 64, further comprising a member disposed within the housing facing the permeable membrane, wherein the separation element and process fluid being arranged to rotate relative to one another comprises arranging the member to rotate relative to the separation element.

67. The shear separation system of claim 64, further comprising a member disposed within the housing facing the permeable membrane, wherein the separation element is arranged to rotate relative to the member.

68. The shear separation system of claim 64, wherein the separation element is stationary.

69. The shear separation system of claim 61, wherein the separation element is stationary.

70. The shear separation system of claim 61, wherein the permeable membrane has a pore size or molecular weight cutoff greater than the size of the substances to be retained on the upstream surface of the membrane.

71. The shear separation system of claim 61, wherein the separation element and the process fluid being arranged to create a turbulent flow includes creating a shear flow boundary layer having a viscous sublayer adjacent to the upstream surface of the permeable membrane and wherein the permeable membrane surface roughness is less than about one fifth the viscous sublayer thickness.

72. The shear separation system of claim 61 wherein the permeable membrane has a pore size of about 1000 kD or less.

73. The shear separation system of claim 72 wherein the permeable membrane has a pore size of about 500 kD or less.

74. A method for controlling a shear separation system comprising:
 generating a permeate flow through a permeable membrane;
 creating a turbulent flow of process fluid across the permeable membrane including generating a shear flow having a shear rate of about 100,000 sec$^{-1}$ or more;
 generating a permeate drag on substances in the process fluid;
 generating a shear lift on the substances in the process fluid;
 balancing the permeate drag and shear lift to establish a separation cutoff size; and
 adjusting at least one of the shear lift and permeate drag to control the separation cutoff size.

75. The method of claim 74 further comprising sensing a parameter indicative of the size of the substances and adjusting at least one of the permeate flow and shear flow.

76. The method of claim 75, wherein sensing a parameter indicative of the size of the substances includes sensing a particle size.

77. The method of claim 74, wherein generating a shear lift includes flowing a process fluid across the surface of a separation element.

78. The method of claim 77, wherein adjusting at least one of the shear lift and the permeate drag includes adjusting the flow rate of the process fluid across the surface of the separation element.

79. The method of claim 74, wherein generating a shear lift includes relatively rotating a separation element and a process fluid.

80. The method of claim 79, wherein adjusting at least one of the shear lift and the permeate drag includes adjusting the relative rotation of the separation element and process fluid.

81. The method of claim 74, wherein adjusting at least one of the shear lift and the permeate drag includes adjusting the permeate flow rate.

82. The method of claim 74 wherein generating a permeate flow through a permeable membrane and creating a turbulent flow of process fluid across a permeable membrane include establishing a permeate flow velocity which is less than about one hundredth of the tangential flow velocity.

83. The method of claim 74 wherein generating a permeate flow through a permeable membrane includes generating a permeate flow through a permeable membrane having a pore size of about 1000 kD or less.

84. The method of claim 83 wherein generating a permeate flow through a permeable membrane includes generating a permeate flow through a permeable membrane having a pore size of about 500 kD or less.

85. A shear separation system comprising:
 a dynamic filter assembly including a permeable membrane, the dynamic filter assembly being capable of generating a shear flow of process fluid having a shear rate of about 100,000 sec$^{-1}$ or more and capable of separating substances of varying size in the process fluid in accordance with shear lift and permeate drag forces on the substances; and
 a controller coupled to the dynamic filter assembly to adjust at least one of the shear lift and the permeate drag forces to balance the permeate drag force and shear lift to control the separation cutoff size.

86. The shear separation system of claim 85, further comprising a sensor coupled to the dynamic filtration assembly and the controller, wherein the sensor senses a parameter indicative of the size of the substances.

87. The shear separation system of claim 85, wherein the dynamic filter assembly includes a housing rotatable relative to a separation element.

88. The shear separation system of claim 85, wherein the dynamic filter assembly includes a separation element rotatable relative to a housing.

89. The shear separation system of claim 85, wherein the dynamic filter assembly includes a member and a separation element disposed within a housing, said member facing an upstream surface of the separation element, said member arranged to rotate relative to the separation element.

90. The shear separation system of claim 85, wherein the dynamic filter assembly includes a member and a separation element disposed within a housing, said member facing an upstream surface of the separation element, said separation element arranged to rotate relative to the member.

91. The shear separation system of claim 85 wherein the permeable membrane has a pore size of about 1000 kD or less.

92. The shear separation system of claim 91 wherein the permeable membrane has a pore size of about 500 kD or less.

* * * * *